US012806245B2

United States Patent

Preston et al.

(12) United States Patent
(10) Patent No.: US 12,806,245 B2
(45) Date of Patent: Nov. 24, 2026

(54) HEMOSTATIC AGENT AND USES THEREOF

(71) Applicant: ROYAL COLLEGE OF SURGEONS IN IRELAND, Dublin (IE)

(72) Inventors: Roger Preston, Dublin (IE); James O'Donnell, Dublin (IE); Hannah Rushe, Dublin (IE)

(73) Assignee: ROYAL COLLEGE OF SURGEONS IN IRELAND, Dublin (IE)

( * ) Notice: Subject to any disclaimer, the term of this patent is extended or adjusted under 35 U.S.C. 154(b) by 1092 days.

(21) Appl. No.: 17/782,924

(22) PCT Filed: Dec. 2, 2020

(86) PCT No.: PCT/EP2020/084333
§ 371 (c)(1),
(2) Date: Jun. 6, 2022

(87) PCT Pub. No.: WO2021/115886
PCT Pub. Date: Jun. 17, 2021

(65) Prior Publication Data

US 2023/0052168 A1 Feb. 16, 2023

(30) Foreign Application Priority Data

Dec. 8, 2019 (EP) .................................... 19214319

(51) Int. Cl.

| | |
|---|---|
| ***A61K 38/00*** | (2006.01) |
| ***A61K 38/17*** | (2006.01) |
| ***A61K 38/36*** | (2006.01) |
| ***A61K 48/00*** | (2006.01) |
| ***A61P 7/04*** | (2006.01) |

(52) U.S. Cl.
CPC .......... *A61K 38/1774* (2013.01); *A61K 38/36* (2013.01); *A61K 38/366* (2013.01); *A61K 48/0058* (2013.01); *A61K 48/0066* (2013.01); *A61P 7/04* (2018.01)

(58) Field of Classification Search
CPC ................................. A61K 38/00; A61P 7/04
See application file for complete search history.

(56) References Cited

U.S. PATENT DOCUMENTS

| | | | | |
|---|---|---|---|---|
| 5,695,993 | A | 12/1997 | Fukudome et al. | |
| 2012/0178693 | A1* | 7/2012 | Light et al. ............ | A61K 38/17 514/14.7 |
| 2014/0030247 | A1 | 1/2014 | Madison et al. | |
| 2018/0244730 | A1* | 8/2018 | Howarth ............ | C07K 14/3156 |

FOREIGN PATENT DOCUMENTS

| | | | |
|---|---|---|---|
| EP | 1905781 | A2 | 4/2008 |
| WO | 2011026000 | A1 | 3/2011 |
| WO | 2014085596 | A1 | 6/2014 |

OTHER PUBLICATIONS

Lattenist et al. (2016) "Renal endothelial protein C receptor expression and shedding during diabetic nephropathy" Journal of Thrombosis and Haemostasis, 14(6), 1171-1182. (Year: 2016).*
López-Sagaseta et al. (2009) "Recombinant expression of biologically active murine soluble EPCR" Protein expression and purification, 64(2), 194-197. (Year: 2009).*
Invitrogen, "pPICZα A, B, and C: Pichia expression vectors for selection on Zeocin™ and purification of secreted, recombinant proteins", User Manual, Cat. No. V195-20, Rev. Date: Jul. 7, 2010, Manual part No. 25-0150, 48 pages. (Year: 2010).*
Mingozzi et al. (2011) "Therapeutic in vivo gene transfer for genetic disease using AAV: progress and challenges" Nature reviews genetics, 12(5), 341-355. (Year: 2011).*
Loughran et al. (2006) "Modified His-tag fusion vector for enhanced protein purification by immobilized metal affinity chromatography" Analytical biochemistry, 355:148-150. (Year: 2006).*
Stearns-Kurosawa et al. "Plasma levels of endothelial protein C receptor respond to anticoagulant treatment." Blood, The Journal of the American Society of Hematology 99(2): 526-530 (2002).
International Search Report and Written Opinion Application No. PCT/EP2020/084333 dated Mar. 23, 2021; pp. 14.

* cited by examiner

*Primary Examiner* — James Joseph Graber
(74) *Attorney, Agent, or Firm* — Nixon Peabody LLP; David S. Resnick; Ravinderjit S. Braich

(57) ABSTRACT

An isolated recombinant soluble endothelial cell protein C receptor (r-sEPCR) for use as a hemostatic agent.

9 Claims, 5 Drawing Sheets

Specification includes a Sequence Listing.

SEQUENCE LISTING

```
<160> NUMBER OF SEQ ID NOS: 17

<210> SEQ ID NO 1
<211> LENGTH: 630
<212> TYPE: DNA
<213> ORGANISM: Homo sapiens

<400> SEQUENCE: 1

atgctgacca ccctgctgcc tattctgctg ctgagcggat gggccttttg ttcacaggac      60

gcaagcgatg gactgcagag actgcacatg ctgcagatct cttacttcag ggacccttac     120
```

```
cacgtgtggt atcagggaaa cgccagcctg ggaggacacc tgacccacgt gctggagggc    180

ccagatacaa ataccacaat catccagctg cagccactgc aggagccaga gagctgggca    240

aggacccagt ccggcctgca gtcttatctg ctgcagtttc acggcctggt gcggctggtg    300

caccaggaga gaaccctggc cttccccctg acaatcaggt gctttctggg ctgtgagctg    360

ccacctgagg gctcccgcgc acacgtgttc tttgaggtgg ccgtgaacgg cagctccttc    420

gtgtccttta ggcctgagcg cgccctgtgg caggcagaca cccaggtgac atctggcgtg    480

gtgaccttca cactgcagca gctgaacgcc tacaatcgga ccagatatga gctgcgggag    540

tttctggagg atacatgcgt gcagtacgtg cagaagcaca tcagcgccga gaataccaag    600

ggctcccaga catctagaag ctatacatcc                                     630
```

```
<210> SEQ ID NO 2
<211> LENGTH: 210
<212> TYPE: PRT
<213> ORGANISM: Homo sapiens

<400> SEQUENCE: 2

Met Leu Thr Thr Leu Leu Pro Ile Leu Leu Leu Ser Gly Trp Ala Phe
1               5                   10                  15

Cys Ser Gln Asp Ala Ser Asp Gly Leu Gln Arg Leu His Met Leu Gln
            20                  25                  30

Ile Ser Tyr Phe Arg Asp Pro Tyr His Val Trp Tyr Gln Gly Asn Ala
        35                  40                  45

Ser Leu Gly Gly His Leu Thr His Val Leu Glu Gly Pro Asp Thr Asn
    50                  55                  60

Thr Thr Ile Ile Gln Leu Gln Pro Leu Gln Glu Pro Glu Ser Trp Ala
65                  70                  75                  80

Arg Thr Gln Ser Gly Leu Gln Ser Tyr Leu Leu Gln Phe His Gly Leu
                85                  90                  95

Val Arg Leu Val His Gln Glu Arg Thr Leu Ala Phe Pro Leu Thr Ile
            100                 105                 110

Arg Cys Phe Leu Gly Cys Glu Leu Pro Pro Glu Gly Ser Arg Ala His
        115                 120                 125

Val Phe Phe Glu Val Ala Val Asn Gly Ser Ser Phe Val Ser Phe Arg
    130                 135                 140

Pro Glu Arg Ala Leu Trp Gln Ala Asp Thr Gln Val Thr Ser Gly Val
145                 150                 155                 160

Val Thr Phe Thr Leu Gln Gln Leu Asn Ala Tyr Asn Arg Thr Arg Tyr
                165                 170                 175

Glu Leu Arg Glu Phe Leu Glu Asp Thr Cys Val Gln Tyr Val Gln Lys
            180                 185                 190

His Ile Ser Ala Glu Asn Thr Lys Gly Ser Gln Thr Ser Arg Ser Tyr
        195                 200                 205

Thr Ser
    210


<210> SEQ ID NO 3
<211> LENGTH: 642
<212> TYPE: DNA
<213> ORGANISM: Mus musculus

<400> SEQUENCE: 3

atgctgacaa agtttctgcc cctgctgctg ctgctgctgc ctggatgtgc cctgtgcaat     60

tctgatggct cccagtctct gcatatgctg cagatctctt acttccagga caaccaccac    120
```

```
gtgcggcacc agggaaatgc ctccctgggc aagctgctga cccacacact ggagggcccc    180

tctcagaacg tgaccatcct gcagctgcag ccctggcagg atcctgagtc ttgggagaga    240

accgagagcg gcctgcagat ctacctgaca cagtttgagt ccctggtgaa gctggtgtat    300

cgggagagaa aggagaacgt gttcttccct ctgaccgtga gctgctccct gggctgtgag    360

ctgccagagg aggaggagga gggaagcgag ccacacgtgt tctttgacgt ggccgtgaac    420

ggctccgcct tcgtgtcttt taggcctaag acagccgtgt gggtgtctgg cagccaggag    480

ccatccaagg ccgccaattt caccctgaag cagctgaacg cctacaatag gacacgctat    540

gagctgcagg agttcctgca ggatacctgc gtggagtttc tggagaacca catcaccaca    600

cagaatatga agggcagcca gacaggcaga tcctatacat cc                      642
```

<210> SEQ ID NO 4
<211> LENGTH: 214
<212> TYPE: PRT
<213> ORGANISM: Mus musculus

<400> SEQUENCE: 4

```
Met Leu Thr Lys Phe Leu Pro Leu Leu Leu Leu Leu Leu Pro Gly Cys
1               5                   10                  15

Ala Leu Cys Asn Ser Asp Gly Ser Gln Ser Leu His Met Leu Gln Ile
            20                  25                  30

Ser Tyr Phe Gln Asp Asn His His Val Arg His Gln Gly Asn Ala Ser
        35                  40                  45

Leu Gly Lys Leu Leu Thr His Thr Leu Glu Gly Pro Ser Gln Asn Val
    50                  55                  60

Thr Ile Leu Gln Leu Gln Pro Trp Gln Asp Pro Glu Ser Trp Glu Arg
65                  70                  75                  80

Thr Glu Ser Gly Leu Gln Ile Tyr Leu Thr Gln Phe Glu Ser Leu Val
                85                  90                  95

Lys Leu Val Tyr Arg Glu Arg Lys Glu Asn Val Phe Phe Pro Leu Thr
            100                 105                 110

Val Ser Cys Ser Leu Gly Cys Glu Leu Pro Glu Glu Glu Glu Glu Gly
        115                 120                 125

Ser Glu Pro His Val Phe Phe Asp Val Ala Val Asn Gly Ser Ala Phe
    130                 135                 140

Val Ser Phe Arg Pro Lys Thr Ala Val Trp Val Ser Gly Ser Gln Glu
145                 150                 155                 160

Pro Ser Lys Ala Ala Asn Phe Thr Leu Lys Gln Leu Asn Ala Tyr Asn
                165                 170                 175

Arg Thr Arg Tyr Glu Leu Gln Glu Phe Leu Gln Asp Thr Cys Val Glu
            180                 185                 190

Phe Leu Glu Asn His Ile Thr Thr Gln Asn Met Lys Gly Ser Gln Thr
        195                 200                 205

Gly Arg Ser Tyr Thr Ser
    210
```

<210> SEQ ID NO 5
<211> LENGTH: 705
<212> TYPE: DNA
<213> ORGANISM: Artificial Sequence
<220> FEATURE:
<223> OTHER INFORMATION: human-sEPCR Snoop

<400> SEQUENCE: 5
atgctgacca ccctgctgcc tattctgctg ctgagcggat gggccttttg ttcacaggac 60
gcaagcgatg gactgcagag actgcacatg ctgcagatct cttacttcag ggacccttac 120
cacgtgtggt atcagggaaa cgccagcctg ggaggacacc tgacccacgt gctggagggc 180
ccagatacaa ataccacaat catccagctg cagccactgc aggagccaga gagctgggca 240
aggacccagt ccggcctgca gtcttatctg ctgcagtttc acggcctggt gcggctggtg 300
caccaggaga gaaccctggc cttccccctg acaatcaggt gctttctggg ctgtgagctg 360
ccacctgagg gctcccgcgc acacgtgttc tttgaggtgg ccgtgaacgg cagctccttc 420
gtgtccttta ggcctgagcg cgccctgtgg caggcagaca cccaggtgac atctggcgtg 480
gtgaccttca cactgcagca gctgaacgcc tacaatcgga ccagatatga gctgcgggag 540
tttctggagg atacatgcgt gcagtacgtg cagaagcaca tcagcgccga gaataccaag 600
ggctcccaga catctagaag ctatacatcc ggcagcggcg gcagcggcaa gctgggagac 660
atcgagttca tcaaggtcaa caagcatcat catcaccatc atgaa 705

<210> SEQ ID NO 6
<211> LENGTH: 717
<212> TYPE: DNA
<213> ORGANISM: Artificial Sequence
<220> FEATURE:
<223> OTHER INFORMATION: mouse s-EPCR Snoop

<400> SEQUENCE: 6
atgctgacaa agtttctgcc cctgctgctg ctgctgctgc ctggatgtgc cctgtgcaat 60
tctgatggct cccagtctct gcatatgctg cagatctctt acttccagga caaccaccac 120
gtgcggcacc agggaaatgc ctccctgggc aagctgctga cccacacact ggagggcccc 180
tctcagaacg tgaccatcct gcagctgcag ccctggcagg atcctgagtc ttgggagaga 240
accgagagcg gcctgcagat ctacctgaca cagtttgagt ccctggtgaa gctggtgtat 300
cgggagagaa aggagaacgt gttcttccct ctgaccgtga gctgctccct gggctgtgag 360
ctgccagagg aggaggagga gggaagcgag ccacacgtgt tctttgacgt ggccgtgaac 420
ggctccgcct tcgtgtcttt taggcctaag acagccgtgt gggtgtctgg cagccaggag 480
ccatccaagg ccgccaattt caccctgaag cagctgaacg cctacaatag gacacgctat 540
gagctgcagg agttcctgca ggatacctgc gtggagtttc tggagaacca catcaccaca 600
cagaatatga agggcagcca gacaggcaga tcctatacat ccggcagcgg cggcagcggc 660
aagctgggcg acatcgagtt tatcaaagtc aacaagcacc accaccacca tcacgaa 717

<210> SEQ ID NO 7
<211> LENGTH: 234
<212> TYPE: PRT
<213> ORGANISM: Artificial Sequence
<220> FEATURE:
<223> OTHER INFORMATION: human s-EPCR Snoop

<400> SEQUENCE: 7

Met Leu Thr Thr Leu Leu Pro Ile Leu Leu Leu Ser Gly Trp Ala Phe
1 5 10 15

Cys Ser Gln Asp Ala Ser Asp Gly Leu Gln Arg Leu His Met Leu Gln
20 25 30

Ile Ser Tyr Phe Arg Asp Pro Tyr His Val Trp Tyr Gln Gly Asn Ala
35 40 45

Ser Leu Gly Gly His Leu Thr His Val Leu Glu Gly Pro Asp Thr Asn
50 55 60

```
Thr Thr Ile Ile Gln Leu Gln Pro Leu Gln Glu Pro Glu Ser Trp Ala
65                  70                  75                  80

Arg Thr Gln Ser Gly Leu Gln Ser Tyr Leu Leu Gln Phe His Gly Leu
                85                  90                  95

Val Arg Leu Val His Gln Glu Arg Thr Leu Ala Phe Pro Leu Thr Ile
            100                 105                 110

Arg Cys Phe Leu Gly Cys Glu Leu Pro Pro Glu Gly Ser Arg Ala His
        115                 120                 125

Val Phe Phe Glu Val Ala Val Asn Gly Ser Ser Phe Val Ser Phe Arg
    130                 135                 140

Pro Glu Arg Ala Leu Trp Gln Ala Asp Thr Gln Val Thr Ser Gly Val
145                 150                 155                 160

Val Thr Phe Thr Leu Gln Gln Leu Asn Ala Tyr Asn Arg Thr Arg Tyr
                165                 170                 175

Glu Leu Arg Glu Phe Leu Glu Asp Thr Cys Val Gln Tyr Val Gln Lys
            180                 185                 190

His Ile Ser Ala Glu Asn Thr Lys Gly Ser Gln Thr Ser Arg Ser Tyr
        195                 200                 205

Thr Ser Gly Ser Gly Gly Ser Gly Lys Leu Gly Asp Ile Glu Phe Ile
    210                 215                 220

Lys Val Asn Lys His His His His His His
225                 230


<210> SEQ ID NO 8
<211> LENGTH: 238
<212> TYPE: PRT
<213> ORGANISM: Artificial Sequence
<220> FEATURE:
<223> OTHER INFORMATION: mouse s_EPCR Snoop

<400> SEQUENCE: 8

Met Leu Thr Lys Phe Leu Pro Leu Leu Leu Leu Leu Leu Pro Gly Cys
1               5                   10                  15

Ala Leu Cys Asn Ser Asp Gly Ser Gln Ser Leu His Met Leu Gln Ile
            20                  25                  30

Ser Tyr Phe Gln Asp Asn His His Val Arg His Gln Gly Asn Ala Ser
        35                  40                  45

Leu Gly Lys Leu Leu Thr His Thr Leu Glu Gly Pro Ser Gln Asn Val
    50                  55                  60

Thr Ile Leu Gln Leu Gln Pro Trp Gln Asp Pro Glu Ser Trp Glu Arg
65                  70                  75                  80

Thr Glu Ser Gly Leu Gln Ile Tyr Leu Thr Gln Phe Glu Ser Leu Val
                85                  90                  95

Lys Leu Val Tyr Arg Glu Arg Lys Glu Asn Val Phe Phe Pro Leu Thr
            100                 105                 110

Val Ser Cys Ser Leu Gly Cys Glu Leu Pro Glu Glu Glu Glu Glu Gly
        115                 120                 125

Ser Glu Pro His Val Phe Phe Asp Val Ala Val Asn Gly Ser Ala Phe
    130                 135                 140

Val Ser Phe Arg Pro Lys Thr Ala Val Trp Val Ser Gly Ser Gln Glu
145                 150                 155                 160

Pro Ser Lys Ala Ala Asn Phe Thr Leu Lys Gln Leu Asn Ala Tyr Asn
                165                 170                 175

Arg Thr Arg Tyr Glu Leu Gln Glu Phe Leu Gln Asp Thr Cys Val Glu
            180                 185                 190
```

```
Phe Leu Glu Asn His Ile Thr Thr Gln Asn Met Lys Gly Ser Gln Thr
        195                 200                 205

Gly Arg Ser Tyr Thr Ser Gly Ser Gly Gly Ser Gly Lys Leu Gly Asp
    210                 215                 220

Ile Glu Phe Ile Lys Val Asn Lys His His His His His His
225                 230                 235


<210> SEQ ID NO 9
<211> LENGTH: 6
<212> TYPE: PRT
<213> ORGANISM: Artificial Sequence
<220> FEATURE:
<223> OTHER INFORMATION: Linker

<400> SEQUENCE: 9

Gly Ser Gly Gly Ser Gly
1               5


<210> SEQ ID NO 10
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: MISC_FEATURE
<222> LOCATION: (1)..(5)
<223> OTHER INFORMATION: (GGGGS)n where n is 1 or greater

<400> SEQUENCE: 10

Gly Gly Gly Gly Ser
1               5


<210> SEQ ID NO 11
<211> LENGTH: 12
<212> TYPE: PRT
<213> ORGANISM: Artificial Sequence
<220> FEATURE:
<223> OTHER INFORMATION: Linker

<400> SEQUENCE: 11

Gly Ser Ala Gly Ser Ala Ala Gly Ser Gly Glu Phe
1               5                   10


<210> SEQ ID NO 12
<211> LENGTH: 9
<212> TYPE: PRT
<213> ORGANISM: Artificial Sequence
<220> FEATURE:
<223> OTHER INFORMATION: Linker

<400> SEQUENCE: 12

Gly Gly Ser Gly Gly Gly Ser Gly Gly
1               5


<210> SEQ ID NO 13
<211> LENGTH: 6
<212> TYPE: PRT
<213> ORGANISM: Artificial Sequence
<220> FEATURE:
<223> OTHER INFORMATION: Linker

<400> SEQUENCE: 13

Gly Cys Ser Gly Cys Ser
1               5
```

<210> SEQ ID NO 14
<211> LENGTH: 12
<212> TYPE: PRT
<213> ORGANISM: Artificial Sequence
<220> FEATURE:
<223> OTHER INFORMATION: SnoopTag

<400> SEQUENCE: 14

```
Lys Leu Gly Asp Ile Glu Phe Ile Lys Val Asn Lys
1               5                   10
```

<210> SEQ ID NO 15
<211> LENGTH: 36
<212> TYPE: DNA
<213> ORGANISM: Artificial Sequence
<220> FEATURE:
<223> OTHER INFORMATION: SnoopTag

<400> SEQUENCE: 15

```
aaactgggcg atattgaatt tattaaagtg aacaaa                              36
```

<210> SEQ ID NO 16
<211> LENGTH: 112
<212> TYPE: PRT
<213> ORGANISM: Artificial Sequence
<220> FEATURE:
<223> OTHER INFORMATION: SnoopCatcher

<400> SEQUENCE: 16

```
Lys Pro Leu Arg Gly Ala Val Phe Ser Leu Gln Lys Gln His Pro Asp
1               5                   10                  15

Tyr Pro Asp Ile Tyr Gly Ala Ile Asp Gln Asn Gly Thr Tyr Gln Asn
            20                  25                  30

Val Arg Thr Gly Glu Asp Gly Lys Leu Thr Phe Lys Asn Leu Ser Asp
        35                  40                  45

Gly Lys Tyr Arg Leu Phe Glu Asn Ser Glu Pro Ala Gly Tyr Lys Pro
    50                  55                  60

Val Gln Asn Lys Pro Ile Val Ala Phe Gln Ile Val Asn Gly Glu Val
65                  70                  75                  80

Arg Asp Val Thr Ser Ile Val Pro Gln Asp Ile Pro Ala Thr Tyr Glu
                85                  90                  95

Phe Thr Asn Gly Leu His Tyr Ile Thr Asn Glu Pro Ile Pro Pro Lys
            100                 105                 110
```

<210> SEQ ID NO 17
<211> LENGTH: 335
<212> TYPE: DNA
<213> ORGANISM: Artificial Sequence
<220> FEATURE:
<223> OTHER INFORMATION: SnoopCatcher

<400> SEQUENCE: 17

```
aagccgctgc gtggtgccgt gtttagcctg cagaaacagc atcccgacta tcccgatatc     60

tatggcgcga ttgatcagaa tgggacctat caaaatgtgc gtaccggcga agatggtaaa    120

ctgaccttta agaatctgag cgatggcaaa tatcgcctgt ttgaaaatag cgaacccgct    180

ggctataaac cggtgcagaa taagccgatt gtggcgtttc agattgtgaa tggcgaagtg    240

cgtgatgtga ccagcattgt gccgcaggat attccggcta catatgaatt taccaacggt    300

aaacattata tcaccaatga accgataccc cgaaa                               335
```

HEMOSTATIC AGENT AND USES THEREOF

CROSS REFERENCE TO RELATED APPLICATIONS

This Application is a 35 U.S.C. § 371 National Phase Entry of International Patent Application No. PCT/EP2020/084333 filed Dec. 2, 2020, which designates the U.S. and claims benefit of foreign priority under 35 U.S.C. § 119 (b) of EP Application Serial No. 19214319.6 filed Dec. 8, 2019, the contents of which are incorporated herein in their entireties by reference.

FIELD OF THE INVENTION

The invention relates to an agent for use in restoring haemostasis in individuals with defective haemostasis. Specifically, the invention relates to an agent that restores haemostasis by inhibition of both the initiation and activity of a crucial anticoagulant pathway triggered upon vessel injury to control clot size.

BACKGROUND TO THE INVENTION

Bleeding incidence in individuals with severe haemophilia is currently managed by prophylactic recombinant FVIII administration with the aim of maintaining FVIII trough levels >1%. It is, however, often difficult to predict how much and how often replacement factor each patient will require, and patients often need larger or more regular FVIII doses to avoid serious bleeding events. Pertinently, >30% of people with severe haemophilia receiving replacement therapy develop anti-FVIII antibodies that necessitate use of alternative haemostatic strategies to 'bypass' the inhibitory activity of anti-FVIII antibodies. These agents, however, are often expensive, must be administered frequently and exhibit variable efficacy in patients. Recently, novel approaches to stimulate haemostasis in individuals with severe haemophilia have been described, but despite their significant promise, their efficacy and safety remain incompletely characterised in the real-world setting. Consequently, although both inhibitor bypass agents and general haemostatic agents exist and are in clinical use, no single product dominates the market.

Similarly, uncontrolled bleeding remains a significant and unmet morbidity in several clinical settings, such as surgery, childbirth and traumatic injury. For example, major bleeding causes ~40% of deaths associated with major trauma. Furthermore, postpartum haemorrhage (PPH) is the most common form of major obstetric haemorrhage and occurs in up to 18% of live births. PPH is almost certainly underestimated due to difficulty in objective measurements of obstetric bleeding. Recombinant factor VIIa (FVIIa) has shown some efficacy in attenuating bleeding refractory to standard treatment, but existing treatments to restore haemostasis in these settings are often ineffective, expensive and used without strong evidence to support their use.

Protein C is a blood enzyme that is activated in response to clot formation. Once converted to its active form (activated protein C; APC), it has an important role in regulating coagulation, where it acts as a 'brake' on clot formation. The rate of APC generation is dependent upon protein C interaction with its receptor, the endothelial cell protein C receptor (EPCR), which is expressed on the surface of blood vessels and positions protein C for optimal activation by another enzyme-receptor complex (thrombin-thrombomodulin complex). Importantly, however, APC must detach from EPCR to subsequently exert its anticoagulant activity, as binding to EPCR completely prevents APC anticoagulant activity due to the requirement for APC binding to cell surface phospholipids via its γ-carboxyglutamic acid domain, which is blocked by EPCR binding.

Individuals with severe haemophilia A exhibit an increased tendency to bleed uncontrollably after injury. In addition, they are at particular risk of spontaneous bleeding into joints, which in turn increases the likelihood of developing joint disease. This increased bleeding tendency is due to mutation of the FVIII gene, which can result in severely reduced FVIII plasma levels and/or function in blood. Consequently, individuals with severe haemophilia exhibit greatly impaired capacity to form blood clots. Current therapy for individuals with severe haemophilia involves prophylactic recombinant FVIII administration to replace the missing FVIII. Recombinant FVIII prophylaxis is administered intravenously on a thrice-weekly basis due to short plasma FVIII half-life (<12 hours). Recombinant FVIII is also often immunogenic in individuals with severe haemophilia A and leads to the generation of antibody inhibitors that block the function of the administered recombinant FVIII. Both existing and emerging bypass agents possess significant flaws, such as variable efficacy and short half-life (rFVIIa), poorly-defined mechanism of action (FEIBA® (an Anti-Inhibitor Coagulant Complex), rFVIIa), potential immunogenicity (Apcintex™ (an APC-specific serpin)), incompatibility with other haemostatic agents (Hemlibra® (an antibody designed to bring activated factor IX and factor X together)) and may promote thrombosis (Hemlibra®, rFVIIa).

WO 2011/026000 describes fusion proteins that are useful to treat patients with haemorrhages and bleeding disorders. WO 2014/085596 describes a monoclonal antibody that binds to activated Protein C and inhibits anticoagulation activity.

Improved and safe haemostatic biologics would also further enhance treatment of individuals with major bleeding in the absence of inherited haemophilia, such as traumatic coagulopathy. Similarly, PPH represents a significant cause of maternal morbidity and mortality both in Ireland and worldwide. The majority (58%) of maternal deaths due to haemorrhage are deemed to be preventable. Despite this, the safe use of haemostatic agents to restore haemostasis in woman with PPH refractory to standard treatment remains poorly defined and new agents with the potential to limit PPH would be desirable. Consequently, there exists a significant market opportunity to develop drug candidates that promote clotting in individuals with haemophilia, but also those with broad applicability for acquired bleeding disorders for which existing treatments are limited or non-optimal.

It is an object of the subject invention to overcome at least one of the above-mentioned problems.

SUMMARY OF THE INVENTION

To address at least one of the limitations mentioned above, the inventors have developed a new therapeutic approach to restore haemostasis in individuals with defective haemostasis, irrespective of whether bleeding was inherited via haemophilia A or B, or whether acquired via an unrelated medical condition. Instead of seeking to replace factors required for clot formation, the inventors designed a therapy that restores haemostasis by inhibition of both the initiation and activity of a crucial anticoagulant pathway triggered upon vessel injury to control clot size. Although not to be bound by theory, the inventors hypothesised that a recombinant soluble, cell-free form of EPCR (SEPCR) would have dual pro-haemostatic activities in haemophilia plasma mediated via (i) competitive inhibition of EPCR-dependent anticoagulant APC generation and (ii) blockade of APC anticoagulant activity once formed. SEPCR exists naturally in plasma at very low levels (~100 ng/ml) and has no known function.

According to the present invention, there is provided, as set out in the appended claims, an isolated recombinant soluble endothelial cell protein C receptor (r-sEPCR) for use as a hemostatic agent.

In one aspect, the isolated recombinant soluble endothelial cell protein C receptor comprises SEQ ID NOs. 2 or 4, or variant thereof, and a tag. Preferably, the tag is defined by SEQ ID NO. 14, or a variant thereof. In a further aspect, the isolated recombinant soluble endothelial cell protein C receptor further comprises a linker between the tag and either SEQ ID NO. 2 or SEQ ID NO. 4, or a variant thereof.

In one aspect, the isolated recombinant soluble endothelial cell protein C receptor further comprises a his-tag fused to the C-terminal end of the recombinant soluble endothelial cell protein C receptor via a peptide linker. Preferably, the peptide linker is selected from SEQ ID NOs. 9 to 13.

In one aspect, the isolated recombinant soluble endothelial cell protein C receptor is defined by SEQ ID NO. 7 or SEQ ID NO. 8.

In one aspect, there is provided a nucleic acid encoding the recombinant soluble endothelial cell protein C receptor described above.

In one aspect there is provided an expression vector comprising the nucleic acid described above. Preferably, the expression vector is selected from the group consisting of an adenovirus-associated virus (AAV) vector, a retroviral vector, an adenoviral vector, a plasmid, or a lentiviral vector. Preferably, said AAV vector comprises an AAV1, AAV2, AAV3, AAV4, AAV5, AAV6, AAV7, AAV8, AAV9, AAV10, AAV11, Rh10, Rh74 or AAV-2i8 AAV serotype.

Preferably, the expression vector above further comprises an intron, an expression control element, one or more adeno-associated virus (AAV) inverted terminal repeats (ITRs) and/or a filler polynucleotide sequence. More preferably, the intron is within or flanks the nucleic acid encoding FVIII variant, or wherein the expression control element is operably linked to the nucleic acid encoding the recombinant soluble endothelial cell protein C receptor, or wherein the AAV ITR(s) flanks the 5' or 3' terminus of the nucleic acid encoding the recombinant soluble endothelial cell protein C receptor, or wherein the filler polynucleotide sequence flanks the 5' or 3'terminus of the nucleic acid encoding the recombinant soluble endothelial cell protein C receptor.

In one aspect, the expression control element comprises a constitutive or regulatable control element, or a tissue-specific expression control element or promoter. Preferably, the expression control element comprises an element that confers expression in liver. In one aspect, the expression control element comprises a TTR promoter or mutant TTR promoter.

In one aspect, the ITR comprises one or more ITRs of any of: AAV1, AAV2, AAV3, AAV4, AAV5, AAV6, AAV7, AAV8, AAV9, AAV10, AAV11, Rh10, Rh74 or AAV-2i8 AAV serotypes, or a combination thereof.

In one aspect, there is provided a pharmaceutical composition comprising the recombinant soluble endothelial cell protein C receptor described above and a biologically acceptable carrier.

In one aspect, the pharmaceutical composition above is suitable for administration to a subject.

In one aspect, there is provided an isolated recombinant soluble endothelial cell protein C receptor as described above, or the nucleic acid described above, for use in a method of treating a hemostatic disorder.

In one aspect, there is provided an isolated recombinant soluble endothelial cell protein C receptor described above, or the nucleic acid described above, for use in a method of preventing a hemostatic disorder.

In one aspect, the disorder is selected from the group consisting of hemophilia A, hemophilia B, FVII deficiency, Glanzmann's thrombasthenia, Bernard-Soulier syndrome, von Willebrand diseases, bleeding associated with trauma, injury, thrombosis, thrombocytopenia, stroke, coagulopathy, disseminated intravascular coagulation (DIC) and over-anticoagulation treatment disorders.

In one aspect, there is provided a formulation comprising the isolated recombinant soluble endothelial cell protein C receptor described above for use in the method as described above.

In one aspect, the recombinant soluble endothelial cell protein C receptor described above is fused to an antifibrinolytic protein. Preferably, the antifibrinolytic protein includes wild type or engineered forms of soluble thrombomodulin, thrombin activatable fibrinolysis inhibitor, protease nexin-1, plasminogen activator 1 and plasminogen activator 2, and the like. The use of such fusion proteins would further complement h-SEPCR$^{Snoop}$ in maintenance of haemostasis and promotion of clot integrity.

Definitions

In the specification, the term "Tag" should be understood to mean a SnoopTag, which is a domain from *Streptococcus pneumoniae* split to form a peptide and binding protein pair, SnoopTag and SnoopCatcher, which form an isopeptide bond when mixed. The term SnoopCatcher should be understood to mean the binding partner protein to the SnoopTag. The description of the SnoopTag and SnoopCatcher peptide and protein binding partnership, and their variants, are described in detail in WO 2016/193746, which is incorporated herein by reference in its entirety. The SnoopTag/SnoopCatcher pairing enables fusion of polypeptides with extremely high affinity. In this instance, the SnoopTag is attached to sEPCR to enable fusion with other proteins with different haemostatic properties. However, the SnoopTag itself is not important for the pro-haemostatic activity of sEPCR itself.

Addition of the SnoopTag to h-sEPCR$^{Snoop}$ will allow fusion of sEPCR to any other wild type or engineered proteins expressed with a complementary SnoopCatcher tag. h-SEPCR$^{Snoop}$ can be fused to antifibrinolytic proteins that would further complement h-SEPCR$^{Snoop}$ in maintenance of haemostasis and promotion of clot integrity. Potential fusion partners would include wild type or engineered forms of soluble thrombomodulin, thrombin activatable fibrinolysis inhibitor, protease nexin-1, plasminogen activator 1 and plasminogen activator 2, and the like.

As used herein, the term "his-tag" or a "polyhistidine tag" is understood to mean a string of histidine residues at either the N- or C-terminus of a recombinant protein. There can be from four to ten residues in a string, although commonly there are six histidine residues.

In the specification, the term "linker" should be understood to mean a short amino acid sequence to separate two or more domains or proteins. Examples of linkers that are commonly used when producing a recombinant protein are GSGGSG (SEQ ID NO. 9), (GGGGS)n (SEQ ID NO. 10), GSAGSAAGSGEF (SEQ ID NO. 11), GGSGGGSGG (SEQ ID NO. 12), or any linker appropriate and known to the skilled person.

As used herein, the term "dysregulated haemostasis" should be understood to mean where the ability of the subject to prevent excessive blood loss and induce thrombus formation is abnormal such that excessive bleeding or excessive thrombosis occurs.

As used herein, the term "subject" or "patient" or refers to any mammal. The patient is preferably a human but can also be a mammal in need of veterinary treatment, for example, a cat, a dog, a cow, a horse, a sheep, a goat, a donkey, a horse, a bull, a calf, a lamb, a foal, a kid, a monkey, an ape, a zebra, a giraffe, a lion, a tiger, a cheetah, a lemur, a gibbon, and other mammals commonly found in zoos and wildlife parks.

For administration to a subject, the agents can be provided in pharmaceutically acceptable compositions. These pharmaceutically acceptable compositions comprise a therapeutically effective amount of the agent, formulated together with one or more pharmaceutically acceptable carriers (additives) and/or diluents. The pharmaceutical compositions can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally (e.g. as a nasal spray or suppository); or (9) nasally. Additionally, agents can be implanted into a patient or injected using a drug delivery system. See, for example, Urquhart, et al., Ann. Rev. Pharmacol. Toxicol. 24:199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960. Guidance for formulations can be found in e.g. Remington: The Science and Practice of Pharmacy by Alfonso R. Gelmaro (Ed.) 20th edition: Dec. 15, 2000, Lippincott, Williams $ Wilkins, ISBN: 0683306472.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The amount of agent which can be combined with a carrier material to produce a single dosage form will generally be that amount of the agent which produces a therapeutic effect. Generally, out of one hundred percent, this amount will range from about 0.1% to 99% of agent, preferably from about 5% to about 70%, most preferably from 10% to about 30%.

Formulations suitable for parenteral administration conveniently include sterile aqueous preparation of the active agent which is preferably isotonic with the blood of the recipient. Thus, such formulations may conveniently contain distilled water, 5% dextrose in distilled water or saline. Useful formulations also include concentrated solutions or solids containing the agent which upon dilution with an appropriate solvent give a solution suitable for parental administration above.

For enteral administration, an agent can be incorporated into an inert carrier in discrete units such as capsules, cachets, tablets or lozenges, each containing a predetermined amount of the active agent; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active agent in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active agent with any suitable carrier.

A syrup or suspension may be made by adding the active agent to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations for oral administration may be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including EDTA, citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethylammonio-1-propanesulfonate), Big-CHAPS (N, N-bis(3-D-gluconamidopropyl)-cholamide), chlorobutanol, octoxynol-9, benzyl alcohol, phenols, cresols, and alkyl alcohols. In one embodiment, the oral absorption enhancer may be sodium lauryl sulfate.

As used herein, the term "administer" or "administering" refers to the placement of a composition into a subject by a method or route which results in at least partial localization of the composition at a desired site such that desired effect is produced. An agent or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

The terms "polypeptide," "peptide" and "protein" refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acids.

As used herein, "variant polypeptides" may comprise conservatively substituted sequences, meaning that one or more amino acid residues is replaced by different residues, and that the conservatively substituted polypeptide retains a desired biological activity, that is essentially equivalent to that of the native polypeptide. Examples of conservative substitutions include substitution of amino acids that do not alter the secondary and/or tertiary structure of the polypeptide. Other examples involve substitution of amino acids that have not been evolutionarily conserved. One or more polypeptide sequences from non-human species can be aligned with, for example, human using methods well known to one of ordinary skill in the art to determine which residues are conserved and which tolerate more variability. Advantageously, in some embodiments, these conserved amino acids are not altered when generating conservatively substituted sequences.

Any given amino acid may be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gin and Asn). Other such conservative substitutions, e.g., substitutions of entire regions having similar hydrophobicity characteristics, are well known. For example, sEPCR polypeptides comprising conservative amino acid substitutions can be tested in any one of the assays described herein to confirm that a desired haemostatic activity of a native sEPCR is retained.

Amino acids may be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser(S), Thr (T), Cys (C), Tyr (Y), Asn (N), Gin (Q); (3) acidic: Asp (D), Glu (E); (4) basic: Lys (K), Arg (R), His (H). Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Conservative substitutions may include, for example: Ala into Gly or into Ser; Arg into Lys; Asn into GIn or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into GIn or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analogue thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA, ribosomal DNA and cDNA. Other suitable nucleic acid molecules are RNA, including mRNA, rRNA and tRNA. The nucleic acid molecule can be naturally occurring, as in genomic DNA, or it may be synthetic, i.e., prepared based up human action, or may be a combination of the two. The nucleic acid molecule can also have certain modification such as 2'-deoxy, 2'-deoxy-2'-fluoro, 2'-O-methyl, 2'-O-methoxyethyl(2'-O-MOE), 2'-O-aminopropyl(2'-O-AP), 2'-O-dimethylaminoethyl(2'-O-DMAOE), 2'-O-dimethylaminopropyl(2'-O-DMAP), 2'-O-dimethylaminoethyloxyethyl(2'-O-DMAEOE), or 2'-O—N-methylacetamido (2'-O-NMA), cholesterol addition, and phosphorothioate backbone as described in U.S. patent application No. 20070213292; and certain ribonucleoside that are is linked between the 2'-oxygen and the 4'-carbon atoms with a methylene unit as described in U.S. Pat. No. 6,268,490.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90%. In one embodiment, there is a 100% decrease (e.g. absent level as compared to a reference sample).

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means two standard deviations (2SD) below normal, or lower, concentration of the marker. The term refers to statistical evidence that there is a difference. It is defined as the probability of deciding to reject the null hypothesis when the null hypothesis is actually true. The decision is often made using the p-value.

```
Sequences
(human sEPCR)
                                          SEQ ID NO. 1
ATGGTGACCACCCTGGTGOUTATTGTGGTGGTGAGCGGATGGGCCTTTTG

TTCACAGGACGCAAGCGATGGACTGCAGAGACTGCACATGCTGCAGATCT
```

-continued

```
CTTACTTCAGGGACCCTTACCACGTGTGGTATCAGGGAAACGCCAGCCTG

GGAGGACACCTGACCCACGTGCTGGAGGGCCCAGATACAAATACCACAAT

CATCCAGCTGCAGCCACTGCAGGAGCCAGAGAGCTGGGCAAGGACCCAGT

CCGGCCTGCAGTCTTATCTGCTGCAGTTTCACGGCCTGGTGCGGCTGGTG

CACCAGGAGAGAACCCTGGCCTTCCCCCTGACAATCAGGTGCTTTCTGGG

CTGTGAGCTGCCACCTGAGGGCTCCCGCGCACACGTGTTCTTTGAGGTGG

CCGTGAACGGCAGCTCCTTCGTGTCCTTTAGGCCTGAGCGCGCCCTGTGG

CAGGCAGACACCCAGGTGACATCTGGCGTGGTGACCTTCACACTGCAGCA

GCTGAACGCCTACAATCGGACCAGATATGAGCTGCGGGAGTTTCTGGAGG

ATACATGCGTGCAGTACGTGCAGAAGCACATCAGCGCCGAGAATACCAAG

GGCTCCCAGACATCTAGAAGCTATACATCC

(human sEPCR)
                                          SEQ ID NO. 2
MLTTLLPILLLSGWAFCSQDASDGLQRLHMLQISYFRDPYHVWYQGNASL

GGHLTHVLEGPDTNTTIIQLQPLQEPESWARTQSGLQSYLLQFHGLVRLV

HQERTLAFPLTIRCFLGCELPPEGSRAHVFFEVAVNGSSFVSFRPERALW

QADTQVTSGVVTFTLQQLNAYNRTRYELREFLEDTCVQYVQKHISAENTK

GSQTSRSYTS

(murine sEPCR)
                                          SEQ ID NO. 3
ATGCTGACAAAGTTTCTGCCCCTGCTGCTGCTGCTGCTGCCTGGATGTGC

CCTGTGCAATTCTGATGGCTCCCAGTCTCTGCATATGCTGCAGATCTCTT

ACTTCCAGGACAACCACCACGTGCGGCACCAGGGAAATGCCTCCCTGGGC

AAGCTGCTGACCCACACACTGGAGGGCCCCTCTCAGAACGTGACCATCCT

GCAGCTGCAGCCCTGGCAGGATCCTGAGTCTTGGGAGAGAACCGAGAGCG

GCCTGCAGATCTACCTGACACAGTTTGAGTCCCTGGTGAAGCTGGTGTAT

CGGGAGAGAAAGGAGAACGTGTTCTTCCCTCTGACCGTGAGCTGCTCCCT

GGGCTGTGAGCTGCCAGAGGAGGAGGAGGAGGGAAGCGAGCCACACGTGT

TCTTTGACGTGGCCGTGAACGGCTCCGCCTTCGTGTCTTTTAGGCCTAAG

ACAGCCGTGTGGGTGTCTGGCAGCCAGGAGCCATCCAAGGCCGCCAATTT

CACCCTGAAGCAGCTGAACGCCTACAATAGGACACGCTATGAGCTGCAGG

AGTTCCTGCAGGATACCTGCGTGGAGTTTCTGGAGAACCACATCACCACA

CAGAATATGAAGGGCAGCCAGACAGGCAGATCCTATACATCC

(murine sEPCR)
                                          SEQ ID NO. 4
MLTKFLPLLLLLLPGCALCNSDGSQSLHMLQISYFQDNHHVRHQGNASLG

KLLTHTLEGPSQNVTILQLQPWQDPESWERTESGLQIYLTQFESLVKLVY

RERKENVFFPLTVSCSLGCELPEEEEEGSEPHVFFDVAVNGSAFVSFRPK

TAVWVSGSQEPSKAANFTLKQLNAYNRTRYELQEFLQDTCVEFLENHITT

QNMKGSQTGRSYTS
```

(h-sEPCR$^{Snoop}$)

```
                                          SEQ ID. NO. 5
ATGCTGACCACCCTGCTGCCTATTCTGCTGCTGAGCGGATGGGCCTTTTG

TTCACAGGACGCAAGCGATGGACTGCAGAGACTGCACATGCTGCAGATCT
```

-continued

CTTACTTCAGGGACCCTTACCACGTGTGGTATCAGGGAAACGCCAGCCTG

GGAGGACACCTGACCCACGTGCTGGAGGGCCCAGATACAAATACCACAAT

CATCCAGCTGCAGCCACTGCAGGAGCCAGAGAGCTGGGCAAGGACCCAGT

CCGGCCTGCAGTCTTATCTGCTGCAGTTTCACGGCCTGGTGCGGCTGGTG

CACCAGGAGAGAACCCTGGCCTTCCCCCTGACAATCAGGTGCTTTCTGGG

CTGTGAGCTGCCACCTGAGGGCTCCCGCGCACACGTGTTCTTTGAGGTGG

CCGTGAACGGCAGCTCCTTCGTGTCCTTTAGGCCTGAGCGCGCCCTGTGG

CAGGCAGACACCCAGGTGACATCTGGCGTGGTGACCTTCACACTGCAGCA

GCTGAACGCCTACAATCGGACCAGATATGAGCTGCGGGAGTTTCTGGAGG

ATACATGCGTGCAGTACGTGCAGAAGCACATCAGCGCCGAGAATACCAAG

GGCTCCCAGACATCTAGAAGCTATACATCCGGCAGCGGCGGCAGCGGCAA

GCTGGGAGACATCGAGTTCATCAAGGTCAACAAGCATCATCATCACCATC

ATGAA (m-sEPCR$^{Snoop}$)

SEQ ID NO. 6

ATGCTGACAAAGTTTCTGCCCCTGCTGCTGCTGCTGCCTGGATGTGC

CCTGTGCAATTCTGATGGCTCCCAGTCTCTGCATATGCTGCAGATCTCTT

ACTTCCAGGACAACCACCACGTGCGGCACCAGGGAAATGCCTCCCTGGGC

AAGCTGCTGACCCACACACTGGAGGGCCCCTCTCAGAACGTGACCATCCT

GCAGCTGCAGCCCTGGCAGGATCCTGAGTCTTGGGAGAGAACCGAGAGCG

GCCTGCAGATCTACCTGACACAGTTTGAGTCCCTGGTGAAGCTGGTGTAT

CGGGAGAGAAAGGAGAACGTGTTCTTCCCTCTGACCGTGAGCTGCTCCCT

GGGCTGTGAGCTGCCAGAGGAGGAGGAGGAGGGAAGCGAGCCACACGTGT

TCTTTGACGTGGCCGTGAACGGCTCCGCCTTCGTGTCTTTTAGGCCTAAG

ACAGCCGTGTGGGTGTCTGGCAGCCAGGAGCCATCCAAGGCCGCCAATTT

CACCCTGAAGCAGCTGAACGCCTACAATAGGACACGCTATGAGCTGCAGG

AGTTCCTGCAGGATACCTGCGTGGAGTTTCTGGAGAACCACATCACCACC

ACAGAATATGAAGGGCAGCCAGACAGGCAGATCCTATACATCCGGCAGCG

GCGGAGCGGCAAGCTGGGCGACATCGAGTTTATCAAAGTCAACAAGCACC

ACCACCACCATCACGAA (h-sEPCR$^{Snoop}$)

SEQ ID NO. 7

MLTTLLPILLLSGWAFCSQDASDGLQRLHMLQISYFRDPYHVWYQGNASL

GGHLTHVLEGPDTNTTIIQLQPLQEPESWARTQSGLQSYLLQFHGLVRLV

HQERTLAFPLTIRCFLGCELPPEGSRAHVFFEVAVNGSSFVSFRPERALW

QADTQVTSGVVTFTLQQLNAYNRTRYELREFLEDTCVQYVQKHISAENTK

GSQTSRSYTSGSGGSGKLGDIEFIKVNKHHHHHH (m-sEPCR$^{Snoop}$)

SEQ ID NO. 8

MLTKFLPLLLLLLPGCALCNSDGSQSLHMLQISYFQDNHHVRHQGNASLG

KLLTHTLEGPSQNVTILQLQPWQDPESWERTESGLQIYLTQFESLVKLVY

RERKENVFFPLTVSCSLGCELPEEEEEGSEPHVFFDVAVNGSAFVSFRPK

-continued

TAVWVSGSQEPSKAANFTLKQLNAYNRTRYELQEFLQDTCVEFLENHITT

QNMKGSQTGRSYTSGSGGSGKLGDIEFIKVNKHHHHHH (linker):

SEQ ID NO. 9

GSGGSG (linker):

SEQ ID NO. 10

(GGGGS)n (linker):

SEQ ID NO. 11

GSAGSAAGSGEF (linker):

SEQ ID NO. 12

GGSGGGSGG (linker):

SEQ ID NO. 13

GCSGCS (SnoopTag):

SEQ ID NO. 14

KLGDIEFIKVNK (SnoopTag):

SEQ ID NO. 15 aaactgggcgatattgaatttattaaagtgaacaaa (SnoopCatcher):

SEQ ID NO. 16

KPLRGAVFSLQKQHPDYPDIYGAIDQNGTYQNVRTGEDGKLTFKNLSDGK

YRLFENSEPAGYKPVQNKPIVAFQIVNGEVRDVTSIVPQDIPATYEFTNG

LHYITNEPIPPK (SnoopCatcher):

SEQ ID NO. 17 aagccgctgcgtggtgccgtgtttagcctgcagaaacagcatcccgacta tcccgatatctatggcgcgattgatcagaatgggacctatcaaaatgtgc gtaccggcgaagatggtaaactgacctttaagaatctgagcgatggcaaa tatcgcctgtttgaaaatagcgaacccgctggctataaaccggtgcagaa taagccgattgtggcgtttcagattgtgaatggcgaagtgcgtgatgtga ccagcattgtgccgcaggatattccggctacatatgaatttaccaacggt aaacattatatcaccaatgaaccgataccccgaaa

BRIEF DESCRIPTION OF THE DRAWINGS

The invention will be more clearly understood from the following description of an embodiment thereof, given by way of example only, with reference to the accompanying drawings, in which:

FIG. 4*a* (iii) describes the binding of APC in the presence of an anti-EPCR monoclonal antibody (RCR-252) which blocks APC binding. Similarly, APC binding to endothelial cells (FIG. 4*a* (iv)) was completely impaired by the presence of h-sEPCR$^{Snoop}$ (FIG. 4*a* (v)), whereas the presence of an h-sEPCR$^{Snoop}$ mutant unable to bind to APC was unable to inhibit APC binding (FIG. 4*a* (vi)). The binding of APC to endothelial cells under each condition is summarised in FIG. 4*b*. Cells were then analysed using a FACSCanto II flow cytometer and data analysed using FlowJo software. Statistical analysis of experimental data was performed using one-way ANOVA and Tukey's multiple comparison post hoc analysis. ns signifies non-significant, *** signifies a p value of <0.001. This data indicates that h-sEPCR$^{Snoop}$ suppresses Protein C/APC binding to endothelial cells.

DETAILED DESCRIPTION OF THE DRAWINGS

Materials and Methods

Figure 1:
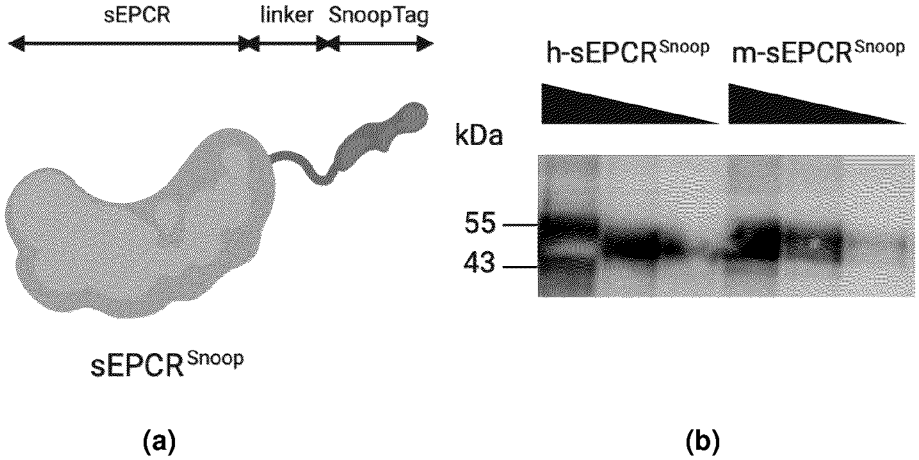
FIG. 1 shows the recombinant expression and purification of human and murine sEPCR$^{Snoop}$: (a) plasmids encoding soluble human and murine EPCR with a 'SnoopTag' and hexapeptide His-tag fused via a peptide linker GSGGSG to the C-terminal end of sEPCR (h-sEPCR$^{Snoop}$ and m-sEPCR$^{Snoop}$) being used to generate lentivirus particles encoding h-sEPCR$^{Snoop}$ and m-sEPCR$^{Snoop}$. h-sEPCR$^{Snoop}$ and m-SEPCR$^{Snoop}$_encoding lentivirus particles were then used to transduce HEK293 cells and transduced cells isolated by puromycin selection. h-sEPCR$^{Snoop}$ and m-SEPCR$^{Snoop}$-expressing HEK293 cells were expanded and incubated with serum-free medium for 5 days, after which the cell supernatant was collected. (b) h-sEPCR$^{Snoop}$ and m-sEPCR$^{Snoop}$ was then purified using nickel ion chromatography, characterised by immunoblotting with an anti-His tag antibody and quantified using human and murine EPCR ELISA.

Lentiviral Expression of Recombinant Human and Murine Soluble EPCR Variants (SEPCR$^{Snoop}$)

Plasmids for the expression of recombinant human and murine sEPCR (SEQ ID NO. 1 and SEQ ID NO. 2, respectively) and of recombinant human and murine sEPCR with the SnoopTag sequence (h-sEPCR$^{Snoop}$ (SEQ ID NO. 5) and m-sEPCR$^{Snoop}$ (SEQ ID NO. 6), respectively) were synthesised and cloned into the lentiviral backbone plasmid pLJM1-Empty (Addgene Plasmid #91980). Both sEPCR constructs were generated with C-terminal hexapeptide His-tags and a 'SnoopTag' sequence (SEQ ID NO. 15) to facilitate fusion with additional protein components with the potential to modulate SEPCR half-life or functional activity. Lentiviral particles were prepared by seeding a 10 $cm^2$ cell culture dish with $5 \times 10^6$ *Lenti*-X HEK293T cells (TakaRa Bio Cat #632180) in 8 mL of cell culture media and incubated overnight at 37° C., 5% $CO_2$. Plasmids encoding h-sEPCR$^{Snoop}$ or m-sEPCR$^{Snoop}$ (7 μg) were mixed with distilled $H_2O$ to make a final volume of 600 μL and added to a *Lenti*-X packaging Single Shot vial (TaKaRa Bio Cat #631276), vortexed and incubated for 10 minutes at room temperature. The solution was then added dropwise to the dish of *Lenti*-X HEK293T cells, the media swirled gently and then incubated for 4 hrs at 37° C. 5% $CO_2$ in a humidified atmosphere. An additional 6 mL of cell media was added and the plate was then incubated for a further 72 hrs for lentivirus particles to be produced. h-sEPCR$^{Snoop}$ and m-sEPCR$^{Snoop}$ lentivirus particles were harvested by removing 13 mL of virus-containing media from the cells and cellular debris cleared by centrifugation for 10 mins at 500×g. The viruses were then concentrated using *Lenti*-X concentrator solution (TaKaRa Bio Cat #631231). One volume of concentrator solution was mixed with three volumes of virus containing supernatant, incubated for 30 mins at 4° C. and centrifuged at 1500×g for 45 minutes. Supernatant was discarded and the virus particles re-suspended in 2 mL of media for transduction of HEK293 cells. Prior to this step, HEK293 cells were seeded at $2 * 10^5$ cells per well into a six well tissue culture plate and incubated overnight. To transduce HEK293 cells with the h-sEPCR$^{Snoop}$ and m-sEPCR$^{Snoop}$ lentiviral particles, cell culture media was removed from the cells and replaced with virus suspension (2 mL) and polybrene (Merck) was added (final concentration, 6 μg/mL) to aid transduction efficiency. Cells were incubated for 24 hrs at 37° C., 5% $CO_2$ before the media was removed and replaced by fresh media. Transduced cells were incubated for a further 72 hrs to allow for plasmid integration. Successfully transduced cells were isolated by antibiotic selection using puromycin-containing cell media (0.6 μg/mL).

SEPCR$^{Snoop}$ Protein Purification and Expression Analysis

Transduced HEK293 cells were seeded in Corning hyper-flasks and grown to confluence, then incubated with serum-depleted cell culture medium for 4-5 days. Cell supernatants were then collected and recombinant h-sEPCR$^{Snoop}$ and m-sEPCR$^{Snoop}$ isolated from cell supernatants by nickel sepharose chromatography. Eluted fractions containing sEPCR$^{Snoop}$ were pooled and concentrated by tangential flow filtration. The presence of sEPCR$^{Snoop}$ was confirmed by immunoblotting and quantified using human and murine sEPCR ELISA (R & D Systems).

Assessment of SEPCR$^{Snoop}$ Inhibition of APC- or TM-Mediated Anticoagulant Activity PPP-Reagent (Thrombinoscope) containing anionic phospholipid vesicles (phosphatidylcholine (PC):, phosphophatidylserine (PS):, phosphatidylethanolamine (PE):, 80:20: 20% ratio, 4 μM) and soluble tissue factor, 5 μM) was used to trigger thrombin generation in platelet-poor pooled normal or factor VIII-deficient human plasma. A thrombin calibrator (Thrombinoscope) was added to enable thrombin quantification. 80 μL of plasma was added to each test well in addition to PPP-Reagent. Activated protein C or thrombomodulin were added as described (see FIGS. 2 and 3) in the presence of h-sEPCR$^{Snoop}$ (1 μM). To start the reaction, 20 μL $Ca^{2+}$ containing saline buffer with a fluorogenic thrombin substrate was added. Thrombin generation was measured for 1 hour using a Flouroskan Ascent plate reader. Analysis of thrombin generation kinetic parameters was performed using Thrombinoscope software.

Assessment of In Vivo Haemostatic Activity of sEPCR in Murine Haemophilia a Model The procoagulant properties of h-sEPCR$^{Snoop}$ can be analysed to determine whether they can be harnessed to drive coagulation in both normal and haemophilia plasma. m-SEPCR$^{Snoop}$ can be assessed for pro-haemostatic activity in vivo using a murine model of haemophilia A (FVIII$^{-/-}$ mice). FVIII$^{-/-}$ mice on a C57BL/6 background are already established within the Royal College of Surgeons in Ireland (RCSI). SEPCR can be evaluated for its ability to attenuate tail bleeding in FVIII$^{-/-}$ mice. Using these mice, a well-characterized assay of bleeding tendency that has been used previously can be utilised to monitor restoration of haemostatic activity (Aljamali M N, Margaritis P, Schlachterman A, et al. J Clin Invest 2008; 118(5): 1825-1834). Briefly, tails of 8-10-week-old FVIII$^{-/-}$ mice are placed in saline for 10 minutes prior to injury. Bleeding is initiated by cutting 2.5 mm from the tip of the tail, whereupon the cut tail is immediately placed in saline. After 5 minutes, m-sEPCR$^{Snoop}$ (0.25-2 mg/kg) or vehicle (n=8 mice per group) is injected as a bolus into the carotid artery, then the tail placed in a new saline-containing container and the extent of bleeding monitored for 30 minutes. Total bleeding time is defined as the sum of the length of bleeding episodes from time of haemostatic agent injection until termination. Blood loss is determined by accumulation of haemoglobin in the saline from the time of treatment. Murine SEPCR (m-sEPCR$^{Snoop}$) can be used here to limit the potential for artefactual species-specific differences in protein C/APC affinity.

Comparison of m-sEPCR$^{Snoop}$ Potency in Restoration of Haemostasis in Haemophilia A Mice Compared to Existing Commercially Available Haemostatic Agents.

The haemostatic potential of sEPCR$^{Snoop}$ compared to recombinant FVIII (the current prophylactic treatment for people with haemophilia A) and recombinant FVIIa (a commonly used pro-haemostatic 'bypass' agent) can be tested using the bleeding models described abobe. To achieve this, sEPCR$^{Snoop}$ can be compared to rFVIII and rFVIIa in their abilities to attenuate tail bleeding in FVIII-mice as described above. 5 minutes after tail clipping, m-sEPCR$^{Snoop}$ (1 mg/kg or alternative effective dose as determined in the previous experiment), rFVIII (50 IU/kg) 34, rFVIIa (1 mg/kg) 35 or vehicle (n=8 mice per group) is injected as a bolus into the carotid artery, the tail is then placed in a new saline-containing container, and the extent of bleeding monitored for 30 minutes and bleeding assessed as previously described.

Assessment of h-sEPCR$^{Snoop}$ Inhibition of Protein C/APC Binding to EPCR on Endothelial Cells EA.hy926 endothelial cells were incubated with FC block for 10 minutes before adding RCR-252 (25 μg/mL), h-sEPCR$^{Snoop}$ (1 μM) or h-sEPCR-E86A$^{Snoop}$ (1 μM), an sEPCR variant unable to bind to PC/APC. The cells were then incubated with fluorescently labelled, biotinylated active-site blocked APC (50 nM). APC-conjugated streptavidin was also added for 30 minutes at 37° C. Cells were then analysed using a FACSCanto II flow cytometer and data analysed using FlowJo software. Statistical analysis of experimental data was performed using one-way ANOVA and Tukey's multiple comparison post hoc analysis. ns signifies non-significant, * signifies a p value of <0.001. This data indicates that h-sEPCR$^{Snoop}$ suppresses Protein C/APC binding to endothelial cells (see FIG. 4**).

Assessment of h-sEPCR$^{Snoop}$ Inhibition of Protein C Activation by the Thrombin-Thrombomodulin Complex on Endothelial Cells Protein C (100 nM) and thrombin (5 nM) were added with h-sEPCR$^{Snoop}$ (1 μM) or h-SEPCR-E86A$^{Snoop}$ (1 μM) an sEPCR variant unable to bind to PC/APC, then incubated for 30 minutes. Thrombin activation was subsequently inhibited using hirudin and APC generation was measured with an APC-specific chromogenic substrate CS-21(66). These data indicate that h-sEPCR$^{Snoop}$ inhibits protein C activation on endothelial cells by the thrombin-thrombomodulin complex and that this activity is dependent on h-sEPCR$^{Snoop}$ binding to PC. The net effect of this restriction of APC generation. Statistical analysis of experimental data was performed using one-way ANOVA and Tukey's multiple comparison post hoc analysis. ns signifies non-significant, * signifies a p value of <0.05 (see FIG. 5).

Discussion

In FIG. 1*a*, we see a schematic diagram of sEPCR$^{Snoop}$, comprised of human/murine EPCR truncated at the membrane spanning region (amino acids 1-219), a short linker region (GCSGCS (SEQ ID NO. 9)) and a SnoopTag (for fusion to other proteins-of-interest, SEQ ID NO. 14). In FIG. 1*b*, human and murine sEPCR$^{Snoop}$ expressed from HEK293 cells into serum-free supernatant and purified using Ni ion chromatography. Both human and murine sEPCR$^{Snoop}$ were visualised by Western blotting using an anti-His horseradish-peroxidase labelled antibody. These data indicate that the expressed SEPCR$^{Snoop}$ protein is expressed normally in a mammalian cell expression system and is present at the anticipated molecular weight.

Figure 2:
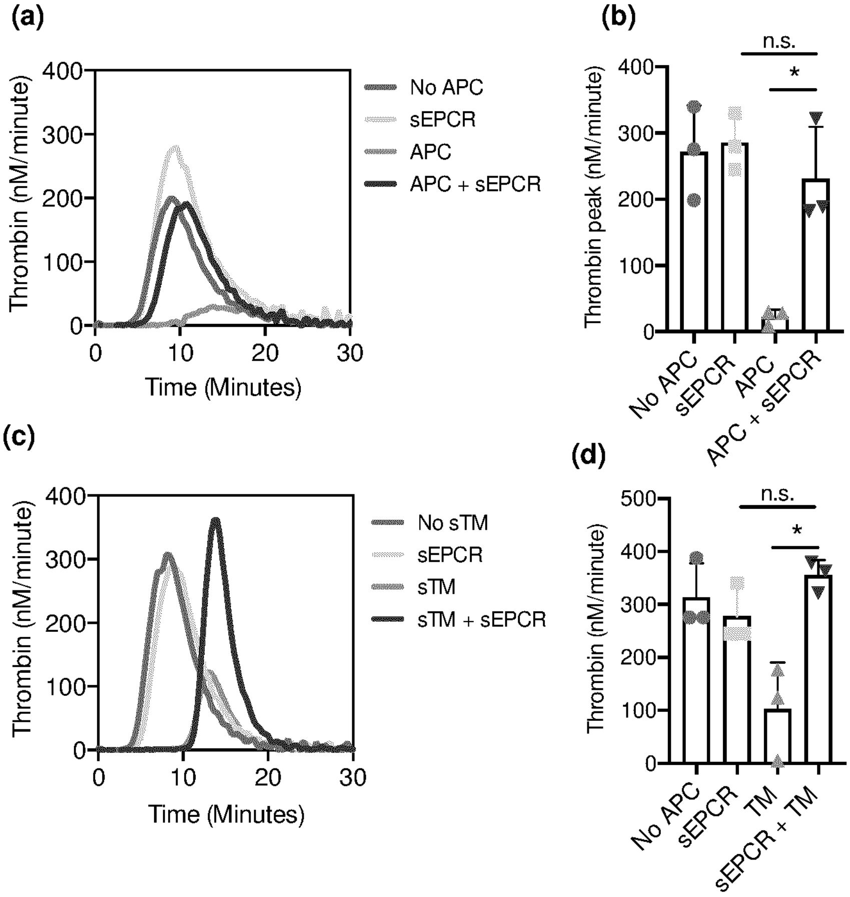
FIG. 2 shows sEPCR-dependent recovery of thrombin generation in normal plasma in the presence of activated anticoagulant protein C pathway: sEPCR-dependent recovery of thrombin generation in normal plasma in the presence of activated anticoagulant protein C pathway. The ability of sEPCR to promote thrombin generation in normal platelet-poor plasma in the presence of either activated protein C (a & b) or soluble thrombomodulin (c & d) was assessed using calibrated automated thrombinography. Briefly, anionic phospholipid vesicles (phosphatidylcholine (PC):, phosphophatidylserine (PS):, phosphatidylethanolamine (PE):, 80:20:20% ratio, 4 μM) and soluble tissue factor (5 μM) was used to trigger thrombin generation. Activated protein C (2.5 nM) or thrombomodulin (5 nM) were added in the presence or absence of h-sEPCR$^{Snoop}$ (1 μM, b & d). Thrombin generation was measured using a Flouroskan Ascent plate reader and analysis of thrombin generation kinetic parameters in each assay was performed using dedicated Thrombinoscope software (thrombin peak, b & d).

FIG. 2 shows the ability of h-sEPCR$^{Snoop}$ to recover thrombin generation in normal platelet-poor plasma in the presence of either (a) APC or (b) TM. Briefly, co-incubation of h-sEPCR$^{Snoop}$ (1 μM) and (a) APC (blue line) is sufficient to overcome the anticoagulant activity of APC alone (gold line). Similarly, h-sEPCR$^{Snoop}$ (1 μM) co-incubated with TM (blue line) is sufficient to overcome the anticoagulant activity of TM alone (gold line). h-sEPCR$^{Snoop}$ restored peak thrombin generation in normal plasma incubated with either APC or TM (b & d). Importantly, h-sEPCR$^{Snoop}$ alone had no effect upon rate and size of thrombin generation in normal plasma. These data indicate that h-sEPCR$^{Snoop}$ can restore thrombin generation in the presence of activated protein C anticoagulant pathway in normal platelet-poor plasma, highlighting its potential as a novel haemostatic agent with application for the treatment of acquired bleeding disorders where the protein C pathway is activated. In addition, these data also indicate that h-sEPCR$^{Snoop}$ alone does not increase thrombin generation in the absence of APC generation, suggesting it is unlikely to possess deleterious prothrombotic properties.

Figure 3:
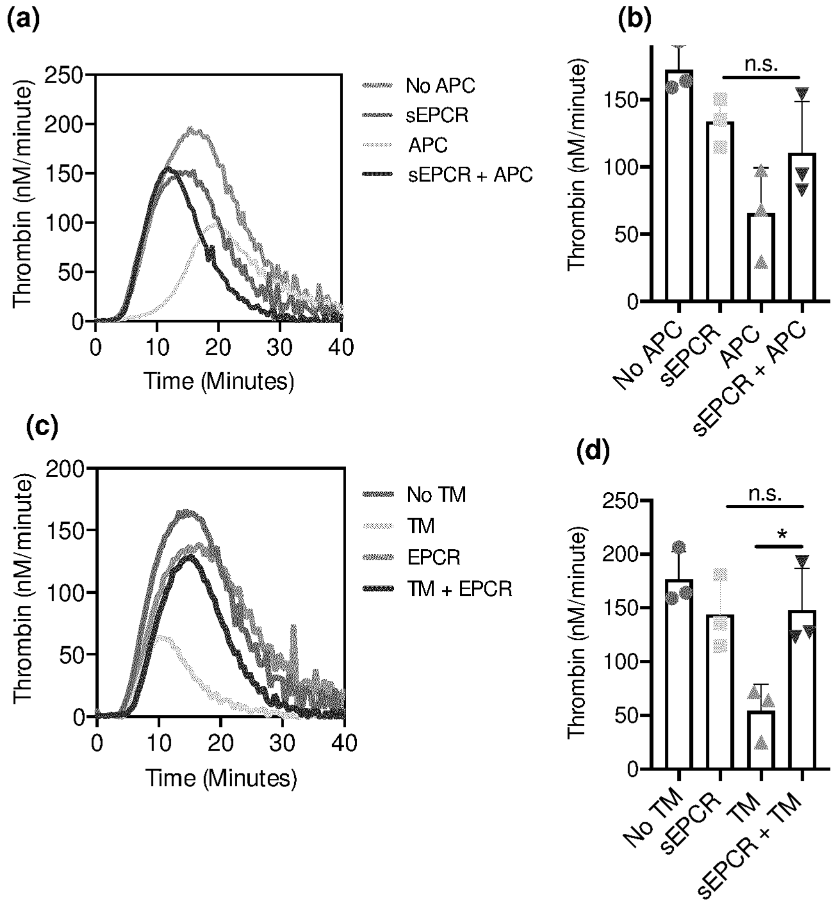
FIG. 3 shows sEPCR-dependent recovery of thrombin generation in factor VIII-deficient plasma in the presence of activated anticoagulant protein C pathway: The ability of sEPCR to promote thrombin generation in platelet-poor factor VIII-deficient plasma in the presence of either activated protein C (a & b) or soluble thrombomodulin (c & d) was assessed using calibrated automated thrombinography. Briefly, anionic phospholipid vesicles (phosphatidylcholine (PC):, phosphophatidylserine (PS):, phosphatidylethanolamine (PE):, 80:20:20% ratio, 4 μM) and soluble tissue factor (5 μM) was used to trigger thrombin generation. Activated protein C (2.5 nM) or thrombomodulin (5 nM) were added in the presence or absence of h-sEPCR$^{Snoop}$ (1 μM, b & d). Thrombin generation was measured using a Flouroskan Ascent plate reader and analysis of thrombin generation kinetic parameters in each assay was performed using dedicated Thrombinoscope software (thrombin peak, b & d).

FIG. 3 also demonstrates that h-sEPCR$^{Snoop}$ can promote recovery of thrombin generation in the presence of either APC (a & b) or TM (c & d) in FVIII-deficient plasma that mimics plasma derived from people with severe haemophilia. Briefly, co-incubation of h-sEPCR$^{Snoop}$ and APC (blue line) is sufficient to overcome the anticoagulant activity of APC alone (gold line). In addition, h-sEPCR$^{Snoop}$ (1 μM) co-incubated with TM (blue line) is sufficient to overcome the anticoagulant activity of TM alone (gold line). h-SEPCR$^{Snoop}$ restored peak thrombin generation in both normal and FVIII-deficient plasma (b & d). Importantly, h-sEPCR alone had no effect upon rate and size of thrombin generation in FVIII-deficient plasma. These data indicate that h-sEPCR$^{Snoop}$ can restore thrombin generation in the presence of activated protein C anticoagulant pathway in platelet-poor FVIII-deficient plasma, highlighting its potential as a novel haemostatic agent with application for the treatment of haemophilia patients with anti-FVIII inhibitors. In addition, similar to experiments in normal platelet-poor plasma, these data also indicate that h-sEPCR$^{Snoop}$ alone does not increase thrombin generation in the absence of APC generation.

Figure 4A:
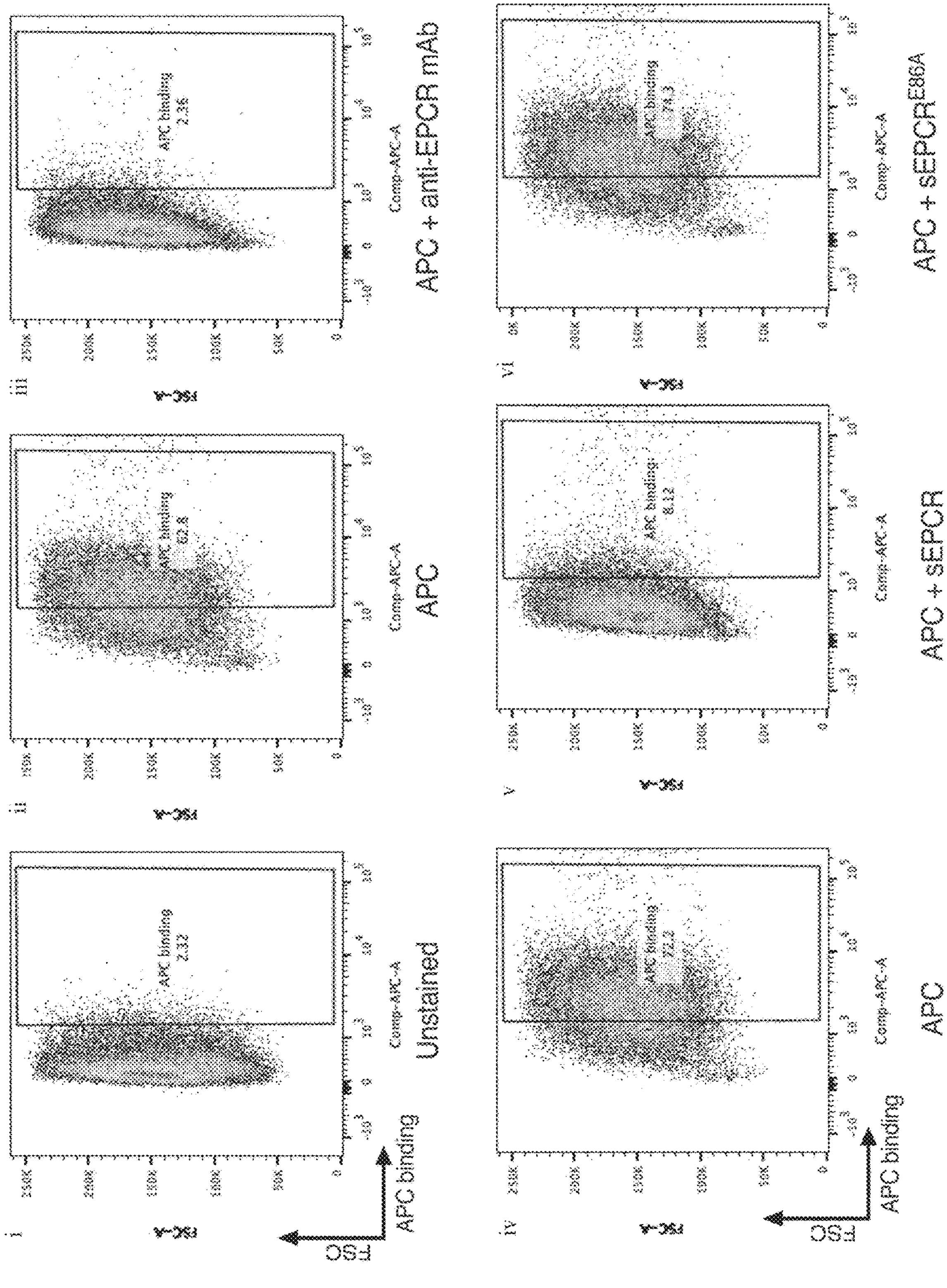
FIG. 4*a* (i) shows live endothelial cells in the absence of APC, whereas FIG. 4*a* (ii) shows APC bound to endothelial cells.
Figure 4B:
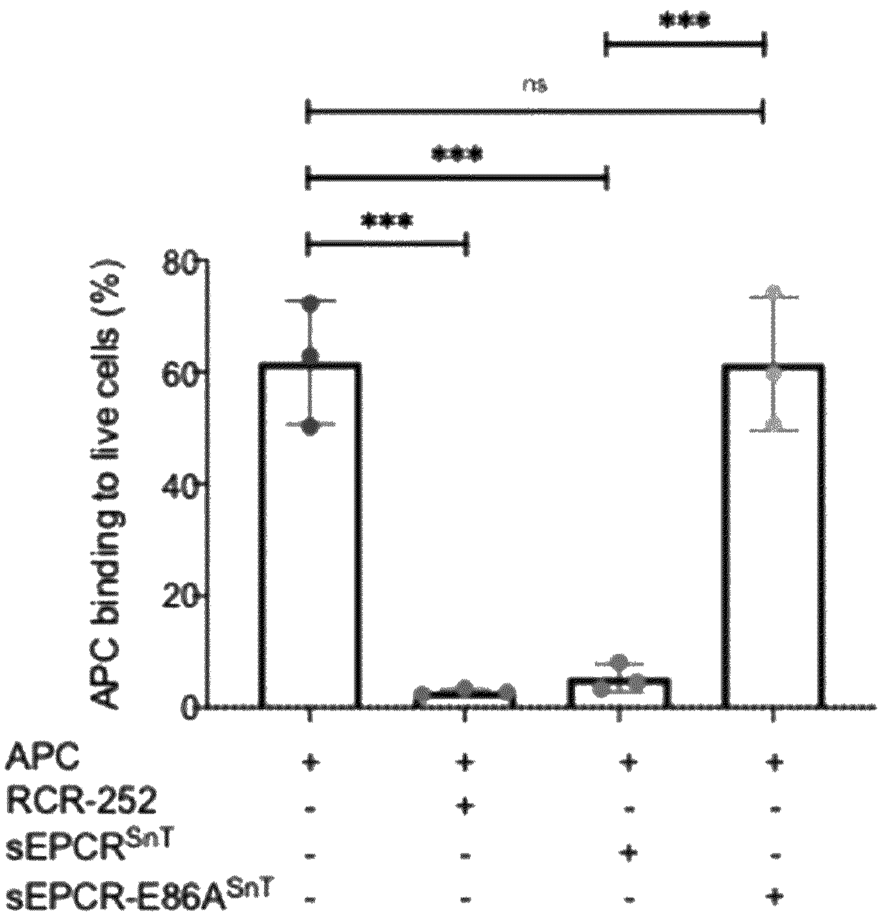
FIG. 4 shows that h-sEPCR$^{Snoop}$ suppresses APC binding to EPCR on endothelial cells. EA.hy926 endothelial cells were incubated with Fc block for 10 minutes before adding RCR-252 (25 μg/mL), h-sEPCR$^{Snoop}$ (1 μM) or h-sEPCR-E86A$^{Snoop}$ (1 μM), an sEPCR variant unable to bind to PC/APC. The cells were then incubated with fluorescently labelled, biotinylated active-site blocked APC (50 nM). APC-conjugated streptavidin was also added for 30 minutes at 37° C.
Figure 5:
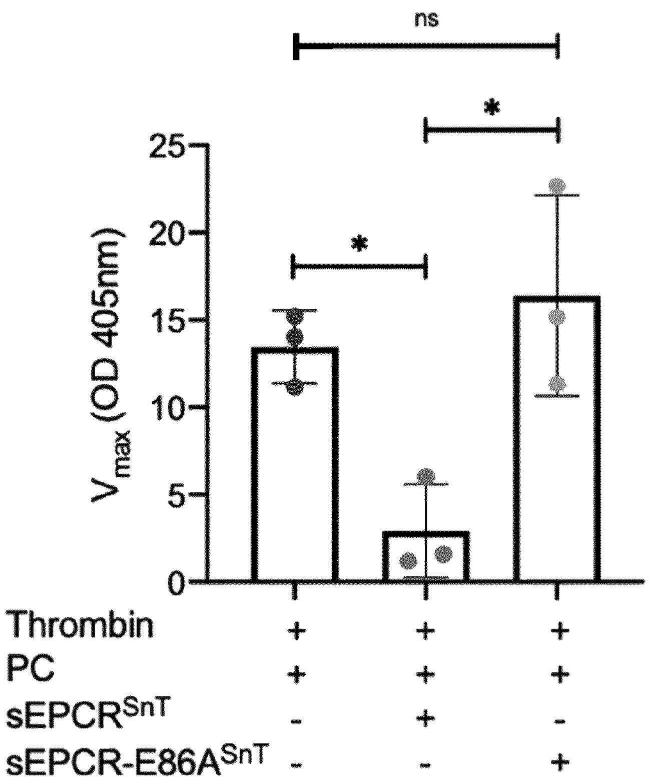
FIG. 5 shows that h-sEPCR$^{Snoop}$ suppresses APC generation on endothelial cells. Protein C (100 nM) and thrombin (5 nM) were added with h-sEPCR$^{Snoop}$ (1 μM) or h-sEPCR-E86A$^{Snoop}$ (1 μM) an sEPCR variant unable to bind to PC/APC, then incubated for 30 minutes. Thrombin activation was subsequently inhibited using hirudin and APC generation was measured with an APC-specific chromogenic substrate CS-21(66). These data indicate that h-sEPCR$^{Snoop}$ inhibits protein C activation on endothelial cells by the thrombin-thrombomodulin complex and that this activity is dependent on h-sEPCR$^{Snoop}$ binding to PC. The net effect of this restriction of APC generation. Statistical analysis of experimental data was performed using one-way ANOVA and Tukey's multiple comparison post hoc analysis. ns signifies non-significant, * signifies a p value of <0.05.

FIG. 4 shows that h-sEPCR$^{Snoop}$ suppresses APC binding to EPCR on endothelial cells, while FIG. 5 indicates that h-sEPCR$^{Snoop}$ inhibits protein C activation on endothelial cells by the thrombin-thrombomodulin complex and that this activity is dependent on h-sEPCR$^{Snoop}$ binding to PC. The net effect of this restriction of APC generation.

It has been previously shown that h-sEPCR$^{Snoop}$ effectively inhibits protein C activation triggered on human endothelial cells, suggesting it can reduce the rate of APC generation. Moreover, the inventors have shown here that sEPCR potently inhibited exogenously administered APC anticoagulant activity in normal pooled plasma. Importantly, h-sEPCR$^{Snoop}$ was also able to completely restore clotting activity in haemophilia A plasma in which endogenous APC was generated, that otherwise demonstrated severely impaired thrombin generation and clotting activity. h-sEPCR$^{Snoop}$ had no independent procoagulant activity in the absence of thrombomodulin or APC.

Furthermore, given that the mode of action of h-sEPCR$^{Snoop}$ is not directly tied to the correction of defective intrinsic tenase activity caused by missing or dysfunctional FVIII, h-sEPCR$^{Snoop}$ may also have utility as a general haemostatic agent in a number of other clinical contexts defined by dysregulated haemostasis.

The claimed invention acts as a soluble decoy receptor to prevent receptor or anionic phospholipid cell surface interactions with zymogen protein C (PC) and APC, respectively. The effect of this interaction is distinct from that described in WO 2014/085596. The claimed invention has shown that h-sEPCR$^{Snoop}$ binds PC or APC equally, and prevents interaction of PC or APC with EPCR on the endothelial cell surface (see FIG. 4). This activity is not described in WO 2014/085596, which binds solely to APC at a distinct molecular location. Inhibition of PC binding to endothelial cell surface EPCR by h-sEPCR$^{Snoop}$ slows generation of APC and in doing so, reduces anticoagulant activity (see FIG. 5). This activity is not described for in WO 2014/085596, which solely impairs APC proteolysis of its procoagulant substrate, activated factor V. sEPCR binding to APC prevents interaction with anionic cell surface phospholipids, preventing complex formation with APC cofactor protein S and activated factor V to attenuate APC anticoagulant activity.

The invention may be used as a means to treat bleeding in haemophilia patients with or without inhibitor antibodies directed against their replacement protein therapy. Furthermore, it may be used to prevent or treat bleeding in individuals with other inherited bleeding disorders (including, but not limited, to factor XI deficiency, factor V deficiency, factor FVII deficiency and factor X deficiency). The invention also illustrates (i) a large-scale recombinant expression system for sEPCR; (ii) an effective dose determination for m-sEPCR$^{Snoop}$ in restricting bleeding in pre-clinical haemophilia models; and (iii) shows a head-to-head pre-clinical efficacy assessment of sEPCR versus commercially available pro-haemostatic therapeutic agents. The invention could also be used as an emergency haemostatic agent that prevents bleeding following trauma or surgery, or to reverse anticoagulant therapy.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described but may be varied in both construction and detail.

What is claimed is:

1. A haemostatic agent comprising a recombinant soluble endothelial cell protein C receptor (r-sEPCR) and a heterologous peptide, wherein the agent comprises the amino acid sequence according to SEQ ID NO: 7 or SEQ ID NO: 8.

2. A nucleic acid encoding a haemostatic agent comprising a recombinant soluble endothelial cell protein C receptor (r-sEPCR) and a heterologous peptide, wherein the agent comprises the amino acid sequence according to SEQ ID NO: 7 or SEQ ID NO: 8.

3. An expression vector comprising a nucleic acid encoding a haemostatic agent comprising a recombinant soluble endothelial cell protein C receptor (r-sEPCR) and a heterologous peptide, wherein the agent comprises the amino acid sequence according to SEQ ID NO: 7 or SEQ ID NO: 8.

4. The expression vector of claim 3, wherein the expression vector is selected from the group consisting of an adenovirus-associated virus (AAV) vector, a retroviral vector, an adenoviral vector, a plasmid, or a lentiviral vector.

5. The expression vector of claim 3, wherein the expression vector is an adenovirus-associated virus (AAV) vector, and wherein the AAV vector comprises an AAV1, AAV2, AAV3, AAV4, AAV5, AAV6, AAV7, AAV8, AAV9, AAV10, AAV11, Rh10, Rh74 or AAV-2i8 AAV serotype.

6. The expression vector of claim 3, wherein the expression vector is an AAV vector comprising an AAV1, AAV2, AAV3, AAV4, AAV5, AAV6, AAV8, AAV9, AAV10, AAV11, Rh10, Rh74 or AAV-2i8 AAV serotype, and further comprises an intron, an expression control element, one or more adeno-associated virus (AAV) inverted terminal repeats (ITRs) and/or a filler polynucleotide sequence.

7. The expression vector of claim 3, wherein the expression vector is an AAV vector comprising an AAV1, AAV2, AAV3, AAV4, AAV5, AAV6, AAV7, AAV8, AAV9, AAV10, AAV11, Rh10, Rh74 or AAV-2i8 AAV serotype, and further comprises an intron, an expression control element, one or more adeno-associated virus (AAV) inverted terminal repeats (ITRs) and/or a filler polynucleotide sequence, wherein the ITR comprises one or more ITRs of any of: AAV1, AAV2, AAV3, AAV4, AAV5, AAV6, AAV7, AAV8, AAV9, AAV10, AAV11, Rh10, Rh74 or AAV-2i8 AAV serotypes, or a combination thereof.

8. The expression vector of claim 3, wherein the expression vector further comprises an expression control element, wherein the expression control element comprises a constitutive or regulatable control element, or a tissue-specific expression control element or promoter.

9. A pharmaceutical composition comprising a haemostatic agent and a biologically acceptable carrier, wherein the haemostatic agent comprises a recombinant soluble endothelial cell protein C receptor (r-sEPCR) and a heterologous peptide, wherein the agent comprises the amino acid sequence according to SEQ ID NO: 7 or SEQ ID NO: 8.

* * * * *